(12) United States Patent
Kawai et al.

(10) Patent No.: US 6,503,232 B1
(45) Date of Patent: Jan. 7, 2003

(54) SHEET PACK

(75) Inventors: Takashi Kawai, Tochigi (JP); Machiko Yokoyama, Tochigi (JP); Manabu Kaneda, Tochigi (JP); Tomohiro Fukita, Tokyo (JP)

(73) Assignee: Kao Corporation, Tokyo (JP)

( * ) Notice: Subject to any disclaimer, the term of this patent is extended or adjusted under 35 U.S.C. 154(b) by 78 days.

(21) Appl. No.: 09/620,554

(22) Filed: Jul. 20, 2000

(30) Foreign Application Priority Data

Sep. 16, 1999 (JP) .......................................... 11-261430
Oct. 13, 1999 (JP) .......................................... 11-291541

(51) Int. Cl.[7] .................. A61F 13/00; A61M 35/00
(52) U.S. Cl. .................. 604/303; 604/289; 604/304; 602/48
(58) Field of Search ................. 604/304, 305, 604/306, 307, 308, 303; 602/41, 42, 48, 57; 424/78.02, 78.03, 78.08, 78.37, 443, 446, 484, 486; 514/844, 847, 944

(56) References Cited

FOREIGN PATENT DOCUMENTS

WO          97/32567     *  9/1997    ................. 424/443

\* cited by examiner

*Primary Examiner*—Kim M. Lewis
(74) *Attorney, Agent, or Firm*—Oblon, Spivak, McClelland, Maier & Neustadt, P.C.

(57) ABSTRACT

A sheet pack includes a moisture-permeable support and a film-forming cosmetic material at least partially supported by the moisture-permeable support. The moisture-permeable support has a yield point in its elongation-stress curve, the stress fi at the yield point is at least about 2 N/50 mm, and the elongation at yield point Si (%) divided by the elongation at break Sb (%) is no more than about 0.8.

20 Claims, 2 Drawing Sheets

SHEET PACK

BACKGROUND OF THE INVENTION

1. Field of the Invention

The present invention relates to a peel-off-type sheet pack.

2. Description of the Related Art

A peel-off pack is a film-forming cosmetic material which is applied to skin, left for a certain period of time to form a film, and then peeled off the skin. Peel-off packs are known in a variety of configurations. With reference to FIG. 3, one of the types most popular because of its convenience is a sheet pack 10 having a multi-layer structure which is composed of a film-forming cosmetic material 4 and a moisture-permeable support 1 consisting of a hydrophilic layer 2 and a water repellent layer 3, wherein the film-forming cosmetic material 4 is supported on the hydrophilic layer 2, and a release sheet 5 is provided over the film-forming cosmetic material 4 as needed (Japanese Patent Application Laid-Open No. H11-12127).

When this sheet pack 10 is shaped to conform to a particular application site, such as the nose, it can be formed in a shape that will readily adhere to the site and afford a high manufacturing yield, as shown in FIG. 4A. When the sheet pack 10 is applied to the skin, it is applied as shown in FIG. 4B after the release sheet 5 is peeled off.

As to the materials from which the sheet pack 10 is formed, from standpoints such as cost and feeling, the hydrophilic layer 2 and the water repellent layer 3 are preferably formed from a hydrophilic nonwoven fabric and water repellent nonwoven fabric, respectively. A known method can be used to join the hydrophilic layer 2 and the water repellent layer 3 to form the moisture-permeable support 1, such as heat embossing, an air-through method, a hydroentangling method, needle punching, or spun bonding. In order to join securely the two layers so that they will not separate, the heat embossing, which can form local fused joints in the hydrophilic layer 2 and the water repellent layer 3, is a preferred method. To give a more specific example of how the moisture-permeable support 1 is manufactured, a mixed fiber layer of polypropylene fibers and rayon fibers is used as the hydrophilic layer 2 and laid over a polypropylene fiber layer that forms the water repellent layer 3, and these layers are joined by heat embossing to form a nonwoven fabric.

The moisture-permeable support 1 must have a certain amount of tensile strength in order to prevent the sheet pack 10 from tearing or leaving behind a sticky residue when the pack 10 is applied to the skin and then peeled away after the film-forming cosmetic material 4 has formed a film. However, in case that the nonwoven fabric that makes up the moisture-permeable support 1 is formed simply by heat embossing, hydroentangling or the like, the sheet pack 10 composed of the moisture-permeable support 1 with adequate tensile strength may not fit well against the external shape of the skin of an application site. In this case, it will be particularly difficult to closely apply the sheet pack 10 to places with three-dimensional shapes such as around the wings of the nose.

SUMMARY OF THE INVENTION

In light of the above problems associated with prior art, it is an object of the present invention to improve the fit of a sheet pack so that the pack can be easily applied to places such as the wings of the nose where conventional packs were difficult to apply.

The inventors found that the moisture-permeable support 1 of a conventional sheet pack 10 does not have a distinct yield point in its tensile characteristics, and consequently, upon receiving an increasing amount of tensile stress, the moisture-permeable support 1 breaks before undergoing sufficient plastic deformation, making it difficult for the pack to fit snugly against the skin. The inventors further found that an effective way of dealing with this is to use a moisture-permeable support in which there is a yield point in the tensile characteristics and in which the ratio between elongation at yield point and elongation at break is within a specific range.

Specifically, the present invention provides a sheet pack comprising a moisture-permeable support and a film-forming cosmetic material at least part of which is supported on the moisture-permeable support, wherein the moisture-permeable support has a yield point in its elongation-stress curve, the stress at the yield point is at least about 2 N/50 mm, and the elongation at yield point (%) divided by the elongation at break (%) is no more than about 0.8.

With the sheet pack of the present invention, the moisture-permeable support that serves as the support for the film-forming cosmetic material has a distinct yield point in its elongation-stress curve, and therefore the moisture-permeable support undergoes plastic deformation very quickly when the sheet pack is subjected to tensile stress above the yield point. Accordingly, it is possible to fit the sheet pack to a place on the skin with any three-dimensional shape by applying tensile stress to the sheet pack.

Furthermore, because the elongation at yield point (%) divided by the elongation at break (%) is no more than about 0.8 with the sheet pack of the present invention, when an increasing amount of tensile stress is applied, the sheet pack undergoes plastic deformation well before it breaks. This makes it possible to fit the sheet pack against the skin easily.

DESCRIPTION OF THE PREFERRED EMBODIMENTS

The present invention will now be described in detail through reference to the Figures. Numbers that are the same in the Figures refer to the same or equivalent constituent elements.

Figure 1:
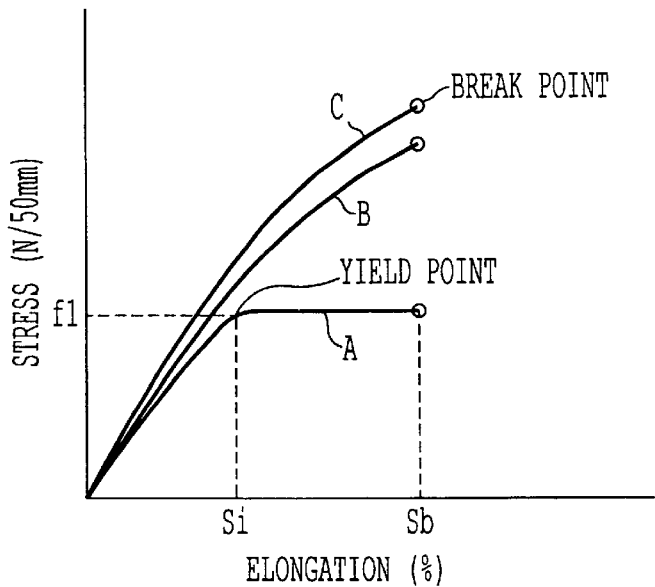
FIG. 1 is a graph illustrating the elongation-stress curve of moisture-permeable supports.

FIG. 1 is a graph of an elongation-stress curve, which illustrates the tensile characteristics of the moisture-permeable support used in the sheet pack of the present invention. In the graph, curve A represents the tensile characteristics of the moisture-permeable support used in the sheet pack of the present invention, curve B is the tensile characteristics of a corresponding moisture-permeable support of a commercially available sheet pack composed of a moisture-permeable support and a film-forming cosmetic material, and curve C is the tensile characteristics of a hydroentangled nonwoven fabric with a soft feeling.

These curves were plotted as follows. A test piece measuring 50 mm×150 mm was put in a tensile tester (Tensilon RTA-100, made by Orientech) and stretched at a temperature of 20° C., a chuck gap of 100 mm, and a pulling rate of 300 mm/min (elongation rate: 200%/min), and the elongation (%) and stress (N/50 mm) were calculated from the formulas (1) and (2) shown below. When a test piece measuring 50×150 mm cannot be obtained, such as when a test piece is taken from a commercially available sheet pack, the test piece is cut as large as possible, a measurement is taken at an elongation rate of 200%/min, and the result is converted into the stress per 50 mm of width of the test piece.

$$\text{Elongation (\%)}=(L_1-L_0)\div L_0 \times 100 \qquad (1)$$

(In the formula, $L_1$ is the test piece length at a given load, and $L_0$ is the test piece length at no load.)

$$\text{Stress (N/50 mm)}=(\text{force (N) applied to test piece})/(\text{width of test piece (50 mm)}) \qquad (2)$$

The "yield point" in the present invention is the point along the elongation-stress curve at which the curve suddenly bends and plastic deformation commences, or the first maximum point appearing on the elongation-stress curve at which plastic deformation commences.

As can be seen in FIG. 1, there is a distinct yield point to the moisture-permeable support used in the present invention (curve A), and at the initial stage of the application of tensile stress there is elasticity or initial rigidity. Accordingly, the moisture-permeable. support used in the present invention (curve A) does not elongate very much and is easy to work in the manufacturing process, but once the tensile stress exceeds the yield point, this support elongates very quickly, following the direction in which the force is applied, without breaking. Therefore, the sheet pack of the present invention fits very well against the skin.

In contrast, the commercially available moisture-permeable support (curve B) and the hydroentangled non-woven fabric (curve C) have no distinct yield point, and break without conforming to the skin when a certain amount of stress is applied. Fit against the skin is therefore poor.

In the present invention, the stress fi at the yield point of the moisture-permeable support is set to be at least about 2.0 N/50 mm, and preferably about 2.5 (N/50 mm)≦fi (N/50 mm)≦about 6 (N/50 mm). This allows the sheet pack to be peeled away from the skin without the sheet pack tearing or leaving behind a sticky residue. The stress at the yield point is a function of the direction in which the moisture-permeable support is placed in the tensile tester during the measurement of the tensile characteristics of a sample of the moisture-permeable support in the tensile tester. In the present invention, when the direction in which the moisture-permeable support is pulled in the tensile tester is matched to the pulling direction of the moisture-permeable support (MD; machine direction) in the production of a roll of this moisture-permeable support material, or to the direction perpendicular thereto (CD; cross direction), the stress fi at the yield point is at least about 2 N/50 mm in at least one of these cases.

With the moisture-permeable support used in the present invention (curve A), the ratio Si/Sb of the elongation at yield point Si (%) to the elongation at break Sb (%) is no more than about 0.8, and preferably no more than about 0.5. As a result, when tensile stress is applied to the sheet pack, the sheet pack undergoes plastic deformation well before breaking. It is therefore easy to fit the sheet pack against the skin.

An example of a moisture-permeable support having the above-mentioned tensile characteristics is a nonwoven fabric formed by both melt joining and fiber entangling.

To form the melt-joined portion of the nonwoven fabric, heat embossing, ultrasonic waves, an air-through method, or the like should be applied to the constituent web of the nonwoven fabric, and to form the entangled fiber portion of the nonwoven fabric, hydroentangling, needle punching, or the like should be applied to the constituent web of the nonwoven fabric. In a preferable method for forming a nonwoven fabric, the melt-joined portion is formed in the constituent web of the nonwoven fabric by heat embossing or an air-through method, and the entangled fiber portion is then formed by hydroentangling. First forming the melt-joined portion and then forming the entangled fiber portion in this manner causes the melt-joined portion formed first to undergo a suitable rubbing treatment, which imparts a softer feeling to the sheet pack.

The moisture-permeable support may be made up of a plurality of layers of nonwoven fabric formed by both melt joining and fiber entangling, or it may be made up of a combination of a nonwoven fabric formed by both melt joining and fiber entangling and another type of nonwoven fabric.

It is preferable for the side of the moisture-permeable support, on which the film-forming cosmetic material is supported, to be formed from a hydrophilic nonwoven fabric, and for the opposite side to be formed from a water repellent nonwoven fabric. This results in the film-forming cosmetic material being supported well by the hydrophilic nonwoven fabric, which prevents the film from tearing or leaving behind a sticky residue. after the pack applied to the skin is peeled away. The water repellent nonwoven fabric prevents the film-forming cosmetic material from oozing out and making the pack surface sticky during the use of the pack.

Figure 2:
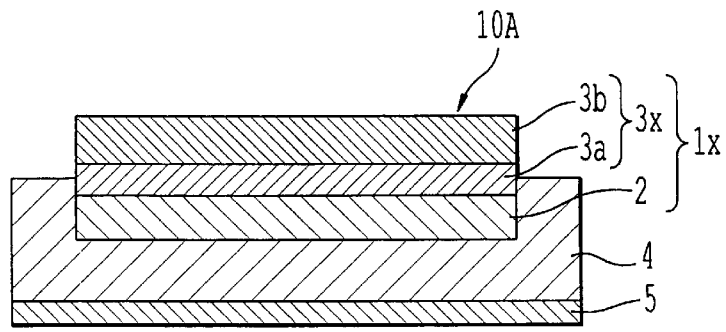
FIG. 2 is a cross section of a sheet pack.
Figure 3:
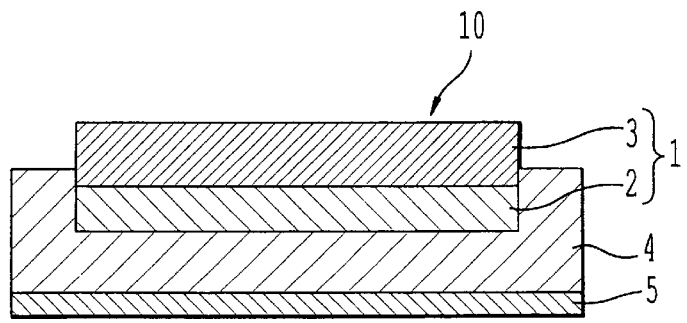
FIG. 3 is a cross section of a sheet pack.

The sheet pack 10A shown in FIG. 2 is a specific example of the multi-layer structure of the sheet pack of the present invention. This sheet pack 10A has a moisture-permeable support 1x formed from a hydrophilic layer 2 composed of a hydrophilic nonwoven fabric and a water repellent layer 3x composed of two layers of water repellent nonwoven fabric (a first water repellent layer 3a and a second water repellent layer 3b), and the film-forming cosmetic material 4 is supported on the hydrophilic layer 2 side of the moisture-permeable support 1x.

Fibrous materials that can be used for the nonwoven fabric that forms the hydrophilic layer 2 here include natural fibers such as cotton, linen, or wool, cellulose-based fibers such as rayon or acetate, or other such hydrophilic fibers; hydrophilic fibers obtained by subjecting water repellent fibers of polyester, polyethylene, polypropylene, polyurethane, or the like to a hydrophilic treatment with a surfactant; and any of these hydrophilic fibers mixed with the above-mentioned water repellent fibers in a proportion such that the mixture as a whole is hydrophilic. Possible configurations of these fibers include single fibers, core/sheath bicomponent fibers, and side-by-side bicomponent fibers.

Fibrous materials that can be used for the nonwoven fabric that forms the first water repellent layer 3a and the second water repellent layer 3b include water repellent synthetic fibers of polyester, polyethylene, polypropylene, polyurethane, or the like, and inorganic fibers. The same fibrous materials may be used for both the nonwoven fabrics of the first water repellent layer 3a and the second water repellent layer 3b, or different materials may be used. Examples of configurations of these fibers include single fibers, core/sheath bicomponent fibers, and side-by-side bicomponent fibers.

There are no particular restrictions on the fiber length or diameter in the webs that form the hydrophilic layer 2, the first water repellent layer 3a, and the second water repellent layer 3b. To enhance the support-ability of the film-forming cosmetic material 4, prevent the film-forming cosmetic material 4 from coming out at the surface on the second water repellent layer 3b side, and soften the overall feeling of the moisture-permeable support 1x, the fiber diameter is preferably about 0.5 to 6 deniers (d), and more preferably about 1 to 5 d.

The moisture-permeable support 1x composed of the hydrophilic layer 2, the first water repellent layer 3a, and the second water repellent layer 3b is formed as follows, for example. First, the fiber layer that forms the hydrophilic layer 2 is laid over the fiber layer that forms the first water repellent layer 3a, and the two layers are joined by heat embossing to form a nonwoven fabric. Next, a fiber layer that will form the nonwoven fabric of the second water repellent layer 3b is positioned over the side of the nonwoven fabric that will serve as the first water repellent layer 3a, and the fibers are entangled by hydroentangling. As such, the formation of an unwoven fabric of the second water repellent layer 3b is performed simultaneously with the joining of the second water repellent layer 3b to the first water repellent layer 3a. As a result, the first water repellent layer 3a has both a melt-joined portion formed by heat embossing and an entangled fiber portion formed by hydroentangling, and the product therefore has the tensile characteristics of the present invention as discussed above.

The basis weight for the moisture-permeable support 1x as a whole is preferably about 15 to 100 g/m$^2$, and more preferably about 20 to 60 g/m$^2$. If the basis weight is less than about 15 g/m$^2$, the film-forming cosmetic material 4 tends to ooze out and be sticky on the side of the moisture-permeable support 1x opposite the side where the film-forming cosmetic material is supported. On the other hand, if about 100 g/m$^2$ is exceeded, the sheet pack 10A will not conform well to the external shape of the skin where it is to be applied, and exceeding this amount is also disadvantageous in terms of cost.

The overall thickness of the moisture-permeable support 1x is preferably about 0.04 to 4 mm, and more preferably about 0.1 to 2 mm, in order to achieve a soft, fluffy feeling while maintaining adequate tensile strength. This thickness is the thickness of the moisture-permeable support 1x under a load of 0.5 g/cm$^2$.

The overall percentage of void of the moisture-permeable support 1x is preferably about 70 to 99%, and more preferably about 85 to 99%. The film-forming cosmetic material 4 will dry too slowly if the percentage of void is less than about 70%, but exceeding about 99% is undesirable because there will be a decrease in the cosmetic film strength when the sheet pack 10A is applied to the skin.

The percentage of void here is the value calculated from the following formula.

Percentage of void (%)=[(ρ−ρ′)/ρ]×100

(ρ is the true specific gravity of the moisture-permeable support, and ρ′ is the apparent specific gravity of the moisture-permeable support.)

The moisture permeability of the moisture-permeable support 1x is preferable about 100 to 10,000 g/m$^2$·24 hrs as measured by the method in JIS Z 0208. If the moisture permeability is less than about 100 g/m$^2$·24 hrs, breathability will be poor, so the film-forming cosmetic material 4 will dry too slowly, but exceeding about 10,000 g/m$^2$·24 hrs is also undesirable because the film-forming cosmetic material 4 will ooze out of the moisture-permeable support 1x when the moisture-permeable support 1x is coated with the film-forming cosmetic material 4 during the manufacture of the sheet pack 10A, which makes the manufacture of the sheet pack 10A difficult.

A variety of film-forming cosmetic materials conventionally used for peel-off packs can be used as the film-forming cosmetic material 4 in the present invention. This material may be in the form of a paste that already contains a sufficient amount of water, or it may start out in dry form, to which water is added at the time of use.

Examples of film-forming agents that can be contained in the film-forming cosmetic material 4 include polyvinyl alcohol, polyvinyl pyrrolidone, polyvinyl formamide, polyvinylacetate emulsion, carboxymethyl cellulose, a maleic anhydride/methyl vinyl ether copolymer, a methyl vinyl ether/vinylacetate copolymer, and a polyvinyl pyrrolidone/vinylacetate copolymer. Examples of thickeners include pectin, gelatin, xanthan gum, carageenan, sodium alginate, pullulan, methyl cellulose, hydroxyethyl cellulose, hydroxypropyl cellulose, and carboxyvinyl polymer.

The film-forming cosmetic material 4 may contain various components such as a humectant, an ingredient for absorption of sebum, or an ingredient for keratotic plug removal, as dictated by the intended application. The sheet pack of the present invention can be used to particular advantage for the removal of keratotic plugs. When the sheet pack of the present invention is used for the removal of keratotic plugs, it is preferable for the film-forming component to be a macromolecular compound having anionic, cationic, or amphoteric salt-forming groups, and more specifically, carboxyl groups, sulfonic acid residues, sulfuric acid residues, phosphoric acid residues, amino groups, ammonium groups, or other such salt-forming groups, as described in the claims of Japanese Patent Application Laid-Open No. H5-97627, so that keratotic plugs in the skin can be removed and peeled away. Among cationic compounds, those containing polymethacryloyloxyethyltrimethylammonium chloride are preferable, and among anionic compounds, those containing sodium polystyrenesulfonate are preferable.

In addition, the film-forming cosmetic material 4 can contain components which are generally used in cosmetic materials, such as whitening components, antiphlogistic components; colorants, pigments, surfactants, preservatives, and disinfectants.

The release sheet 5, such as a sheet composed of polyester, polypropylene, polyethylene or nylon, may be laminated to the surface on the film-forming cosmetic material 4 side as needed. The release sheet 5 is peeled off just before the pack is applied to the skin.

For the sake of tensile strength and ease of application, the overall thickness of the sheet pack 10A is preferably about 50 to 2500 µm, excluding the thickness of the release sheet 5.

Figure 4A:
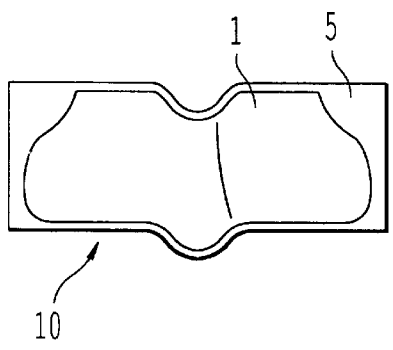
FIG. 4A is a plan view of a sheet pack for the nose and FIG. 4B is a diagram of how this sheet pack is used.
Figure 4B:
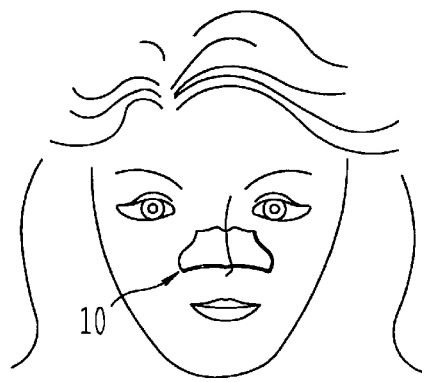

There are no particular restrictions on the external shape of the sheet pack 10A, and the sheet can be made in a suitable width and then cut as needed when applied to the skin. It may also be pre-cut to a shape suited to the forehead, cheek, nose, and so on. For instance, the sheet pack can be shaped for easy application to the nose as shown in FIGS. 4A and 4B.

The sheet pack 10A can be manufactured as follows, for example. The release sheet 5 is coated with the film-forming cosmetic material 4, over which the moisture-permeable support 1x is laid so that the hydrophilic layer 2 of the moisture-permeable support 1x is impregnated with the film-forming cosmetic material 4. In this case, the moisture-permeable support 1x may be pressed with a roller or the like to press it against the release sheet 5 side. Next, if the film-forming cosmetic material 4 is the type that comes in the form of a paste, the sheet pack 10A is adjusted for water content, then cut to a required shape, and stored in a sealed container with no water permeability so that the water will not evaporate before use. If the film-forming cosmetic material 4 is a dry type (in which the water content of the sheet pack 10A, excluding the release sheet 5, is about 0.1 to 30 wt %), then the sheet pack 10A is dried after the hydrophilic layer 2 has been impregnated with the film-forming cosmetic material 4, and then cut to a required shape.

The sheet pack 10A of the present invention has been described in detail above through reference to FIG. 2. In addition to the embodiment illustrated in FIG. 2, various other embodiments of the present invention are also possible, as long as the moisture-permeable support has the above-mentioned tensile characteristics. For instance, the moisture-permeable support may be composed of a single hydrophilic layer and a single water repellent layer, in which the water repellent layer includes a portion melt-joined to the hydrophilic layer, and an entangled fiber portion. Further, with respect to the sheet pack 10A shown in FIG. 2, a third water repellent layer may be further laminated over the second water repellent layer 3b. Also, the hydrophilic layer 2 is not limited to being formed from a single nonwoven fabric, and may instead be formed from a plurality of layers of nonwoven fabric.

EXAMPLES

Example 1

(i) Manufacture of the sheet pack

A two-layer nonwoven fabric (20 g/m$^2$) was manufactured, by heat embossing, from a water repellent nonwoven fabric and a hydrophilic nonwoven fabric. The water repellent nonwoven fabric (first water repellent layer; 10 g/m$^2$) was composed of 100% polypropylene fibers (core/sheath bicomponent fibers, with the melting point of the sheath lower than that of the core). The hydrophilic nonwoven fabric (hydrophilic layer; 10 g/m$^2$) was composed of polypropylene fibers (core/sheath bicomponent fibers, with the melting point of the sheath lower than that of the core) and rayon fibers (mixing ratio: 40%/60%). 100% polyester fibers (20 g/m$^2$; second water repellent layer) were placed over the water repellent layer side of this two-layer nonwoven fabric, and the fibers were entangled by a hydroentangling method, thereby manufacturing a moisture-permeable support (40 g/m$^2$) composed of a three-layer nonwoven fabric including a water repellent hydroentangled nonwoven fabric (second water repellent layer), a water repellent heat embossed nonwoven fabric (first water repellent layer), and a hydrophilic heat embossed nonwoven fabric (hydrophilic layer).

In a vessel equipped with a stirrer, a mixture of 25.0 wt % polymethacryloyloxyethyltrimethylammonium chloride, 15.0 wt % silicic anhydride, 5.0 wt % glycerol, 0.2 wt % polyoxyethylene-hardened castor oil, 0.1 wt % methyl paraben, a trace amount of perfume, and 54.7 wt % purified water was stirred at room temperature to dissolve the components. The solution was deaerated under reduced pressure to prepare a film-forming cosmetic material solution for removal of keratotic plugs.

The film-forming cosmetic material solution was evenly cast in a thickness of approximately 300 μm over a release sheet of a polypropylene film. Immediately after this, the above-mentioned moisture-permeable support was laminated from the hydrophilic layer side. The laminate was passed through an 80° C. hot-air dryer so as to adjust the water content to be 15 to 20 wt % in the sheet pack after the removal of the release sheet. This procedure gave a sheet pack with the layer configuration shown in FIG. 2.

(ii) Evaluation (ii-1) Tensile characteristics

A test piece measuring 50×150 mm was cut out of a moisture-permeable support without supporting a film-forming cosmetic material. Using a tensile tester (Tensilon RTA-100, made by Orientech), the test piece was stretched at a temperature of 20° C., a chuck gap of 100 mm, and a pulling rate of 300 mm/min (elongation rate: 200%/min), and the elongation (%) and stress (N/50 mm) were calculated from Formulas (1) and (2) given above. An elongation-stress curve was plotted, and the stress fi at the yield point was determined. The ratio Si/Sb of the elongation at yield point Si (%) to the elongation at break Sb (%) was also determined. The results are given in Table 1.

(ii-2) Performance evaluation

The sheet pack was subjected to a usage test by a panel. In this usage test, the sheet pack was first cut to the nose shape shown in FIG. 4A. Next, an area of clean skin (where the sheet was to be applied) was first coated with an appropriate amount of water, and the cut sheet pack was pressed against the skin as shown in FIG. 4B. The sheet pack was peeled off after drying. The panel evaluated the sheet pack for ease of application to the entire nose, adhesion to the entire nose, ease of application to the verge of the wings of the nose, adhesion to the verge of the wings of the nose, keratotic plug removal effect from the entire nose, and keratotic plug removal effect from the verge of the wings of the nose by the following evaluation criteria:

(criteria)

A: extremely good

B: good

C: fair

D: poor

The results are given in Table 1.

Example 2

A sheet pack was obtained and evaluated in the same manner as in Example 1, except that an air-through method was used instead of the heat embossing method in the manufacture of the moisture-permeable support in Example 1.

Comparative Example 1

A two-layer nonwoven fabric (25 g/m$^2$) was produced, by heat embossing, from a water repellent nonwoven fabric and a hydrophilic nonwoven fabric. The water repellent nonwoven fabric (water repellent layer; 15 g/m$^2$) was composed of 100% polypropylene fibers (core/sheath bicomponent fibers, with the melting point of the sheath lower than that of the core). The hydrophilic nonwoven fabric (hydrophilic layer; 10 g/m$^2$) was composed of polypropylene fibers (core/sheath bicomponent fibers, with the melting point of the sheath lower than that of the core) and rayon fibers (mixing ratio: 40%/60%). Other than using this product as a moisture-permeable support, a sheet pack was obtained and evaluated in the same manner as in Example 1. The results are given in Table 1.

Comparative Example 2

A sheet pack was obtained and evaluated in the same manner as in Comparative Example 1, except that a hydroentangling method was used instead of the heat embossing method in the manufacture of the moisture-permeable support in Comparative Example 1.

Comparative Example 3

A sheet pack was obtained and evaluated in the same manner as in Comparative Example 1, except that an air-through method was used instead of the heat embossing method in the manufacture of the moisture-permeable support in Comparative Example 1.

TABLE 1

|  | Ex. 1 | Ex. 2 | C. Ex. 1 | C. Ex. 2 | C. Ex. 3 |
|---|---|---|---|---|---|
| Yield point stress fi (N/50 mm) | 4.0 | 4.5 | no yield point | no yield point | no yield point |
| Elongation at yield point Si/elongation at break Sb | 0.30 | 0.35 | 1.00 | 1.00 | 1.00 |
| Method of mfg. moisture-Permeable support | HE + H | AT + H | HE | H | AT |
| Ease of application to the entire nose | A | A | B | B | B |
| Adhesion to the entire nose | A | A | B | B | B |
| Ease of application to the verge of the wings of the nose | A | A | C | C | C |
| Adhesion to the verge of the wings of the nose | A | B | C | C | C |
| Keratotic plug removal effect from entire nose | A | A | B | B | B |
| Keratotic plug removal effect from the verge of wings of the nose | A | B | C | C | C |

[HE: heat embossing; H: hydroentangling; AT: air-through]

It can be seen from Table 1 that good results were obtained in all evaluation categories with Examples 1 and 2, but that ease of application to the verge of wings of the nose, adhesion to the verge of wings of the nose, and keratotic plug removal effect from the the verge of wings of the nose were somewhat inferior with Comparative Examples 1 to 3.

With the sheet pack of the present invention, it is possible to improve the fit against the skin, allowing the pack to be easily fitted tightly even against places where a conventional pack would be difficult to apply, such as the verge of the wings of the nose.

The disclosures of the specifications, claims and drawings of Japanese Patent Applications No. 11-291541 filed on Oct. 13, 1999 and No. 11-261430 filed on Sep. 16, 1999 are hereby incorporated by reference.

What is claimed is:

1. A sheet pack, comprising:
   a moisture-permeable support; and
   a film-forming cosmetic material at least part of which is supported on the moisture-permeable support,
   wherein the moisture-permeable support has a yield point in its elongation-stress curve, stress at the yield point is at least about 2 N/50 mm, and elongation at the yield point (%) divided by elongation at break (%) is no more than about 0.8.

2. The sheet pack according to claim 1, wherein the elongation at the yield point (%) divided by the elongation at break (%) is no more than about 0.5.

3. The sheet pack of claim 1, wherein said moisture-permeable support is comprised of a hydrophilic nonwoven fabric and a water repellent nonwoven fabric.

4. The sheet pack of claim 3, wherein said water repellent nonwoven fabric is comprised of a first water repellent layer and a second water repellent layer.

5. The sheet pack of claim 4, wherein said hydrophilic nonwoven fabric and said first water repellent layer are melt-joined.

6. The sheet pack of claim 5, wherein said layers are melt-joined by a method selected from the group consisting of heat embossing, ultrasonic waves, or an air-through method.

7. The sheet pack of claim 4, wherein said first water repellent layer and said second water repellent layer are joined by fiber entanglement.

8. The sheet pack of claim 7, wherein said fiber entanglement is performed by a method selected from the group consisting of hydroentangling and needle punching.

9. The sheet pack of claim 1, wherein said moisture-permeable support has a basis weight of about 15–100 g/m$^2$.

10. The sheet pack of claim 1, wherein said moisture-permeable support has an overall thickness of about 0.04 to 4 mm.

11. The sheet pack of claim 1, wherein said moisture-permeable support has an overall percentage of volume of about 70–99%.

12. The sheet pack of claim 1, wherein said moisture-permeable support has a moisture permeability of about 100–10,000 g/m$^2$·24 hours.

13. The sheet pack of claim 1, wherein said film-forming cosmetic material is selected from the group consisting of polyvinyl alcohol, polyvinyl pyrrolidone, polyvinyl formamide, polyvinyl acetate emulsion, carboxymethyl cellulose, a maleic anhydride/methylvinyl ether copolymer, a methylvinyl ether/vinyl acetate copolymer, a polyvinyl pyrrolidone/vinyl acetate copolymer and a mixture thereof.

14. The sheet pack of claim 1, wherein said film-forming component is a macromolecular compound having anionic, cationic or amphoteric salt-forming groups.

15. The sheet pack of claim 1, wherein said film-forming component comprises polymethacryloyloxyethyl trimethylammonium chloride.

16. The sheet pack of claim 1, further comprising a release sheet.

17. The sheet pack of claim 4, wherein said film-forming component is supported on said hydrophilic nonwoven fabric.

18. The sheet pack of claim 1, wherein said multilayer moisture-permeable support is produce by successive lamination of a hydrophilic layer, a first water repellent layer, and a second water repellant layer,
   wherein said hydrophilic layer, said first water repellent layer and said second water repellent layer are each comprised of a nonwoven fabric, said hydrophilic layer and said first water repellent layer are joined by melt-joining, said second water repellent layer is formed by fiber entangling; and
   wherein said film-forming cosmetic material is supported by at least said hydrophilic layer.

19. The sheet pack of claim 18, wherein said layers are melt-joined by a method selected from the group consisting of heat embossing, ultrasonic waves, or an air-through method.

20. The sheet pack of claim 18, wherein said fiber entanglement is performed by hydroentangling.

* * * * *